US010624838B2

(12) United States Patent
Lafont et al.

(10) Patent No.: US 10,624,838 B2
(45) Date of Patent: Apr. 21, 2020

(54) USE OF GINGIVAL FIBROBLASTS IN THE TREATMENT OF ALOPECIA

(71) Applicants: ASSISTANCE PUBLIQUE—HOPITAUX DE PARIS, Paris (FR); INSTITUT NATIONAL DE LA SANTE ET DE LA RECHERCHE MEDICALE (INSERM), Paris (FR); INSTITUT DE RADIOPROTECTION ET DE SURETE NUCLEAIRE, Fontenay-aux-Roses (FR); Etat Francais—Ministere de la Defense—Direction centrale du service de sante des armees, Clamart (FR); UNIVERSITE PARIS DESCARTES, Paris (FR)

(72) Inventors: Antoine Lafont, Paris (FR); Bernard Coulomb, Igny (FR); Jean-Jacques Lataillade, Elancourt (FR); Christine Linard, Ris Orangis (FR)

(73) Assignees: ASSISTANCE PUBLIQUE—HOPITAUX DE PARIS, Paris (FR); INSTITUT NATIONAL DE LA SANTE ET DE LA RECHERCHE MEDICALE (INSERM), Paris (FR); INSTITUT DE RADIOPROTECTION ET DE SURETE NUCLEAIRE, Fontenay-aux-Roses (FR); ETAT FRANCAIS—MINISTERE DE AL DEFENSE—DIRECTION CENTRALE DU SERVICE DE SANTE DES ARMEES, Clamart (FR); UNIVERSITE PARIS DESCARTES, Paris (FR)

( * ) Notice: Subject to any disclaimer, the term of this patent is extended or adjusted under 35 U.S.C. 154(b) by 0 days.

(21) Appl. No.: 14/904,151

(22) PCT Filed: Jul. 9, 2014

(86) PCT No.: PCT/EP2014/064772
§ 371 (c)(1),
(2) Date: Jan. 11, 2016

(87) PCT Pub. No.: WO2015/004216
PCT Pub. Date: Jan. 15, 2015

(65) Prior Publication Data
US 2016/0151274 A1   Jun. 2, 2016

(30) Foreign Application Priority Data
Jul. 9, 2013 (FR) ..................................... 13 56740

(51) Int. Cl.
*A61K 8/98* (2006.01)
*A61K 31/505* (2006.01)
*A61K 31/58* (2006.01)
*A61K 35/33* (2015.01)
*A61Q 7/00* (2006.01)

(52) U.S. Cl.
CPC ............ *A61K 8/981* (2013.01); *A61K 31/505* (2013.01); *A61K 31/58* (2013.01); *A61K 35/33* (2013.01); *A61Q 7/00* (2013.01); *A61K 2800/40* (2013.01)

(58) Field of Classification Search
None
See application file for complete search history.

(56) References Cited

U.S. PATENT DOCUMENTS

| 8,119,122 B2 | 2/2012 | Lafont et al. | |
|---|---|---|---|
| 2008/0138324 A1* | 6/2008 | Kleinsek | A61K 38/1808 424/93.7 |
| 2008/0139469 A1* | 6/2008 | Imamura | A61K 8/606 514/9.1 |
| 2008/0254006 A1 | 10/2008 | Hantash et al. | |
| 2010/0166711 A1* | 7/2010 | Gogly | A61F 15/00 424/93.7 |
| 2010/0210530 A1* | 8/2010 | Naughton | A61K 8/982 514/20.1 |
| 2011/0086079 A1* | 4/2011 | Lindner | A61L 27/3604 424/422 |

FOREIGN PATENT DOCUMENTS

| EP | 0455422 A2 | 11/1991 |
|---|---|---|
| EP | 1972685 A1 | 9/2008 |
| FR | 2872431 A1 | 1/2006 |
| WO | 2008017927 A2 | 2/2008 |
| WO | 2009121761 A1 | 10/2009 |

OTHER PUBLICATIONS

Rosenquist, T.A. et al. 1996. Fibroblast growth factor signalling in the hair growth cycle: Expression of the fibroblast growth factor receptor and ligand genes in the murine hair follicle. Developmental Dynamics 205: 379-386. specif. pp. 379, 384.*
Sanaie, A.R. et al. 2002. Keratinocyte growth factor (KGF)-1 and -2 protein and gene expression in human gingival fibroblasts. Journal of Periodontal Research 37: 66-74. specif. p. 66.*
Ota, Y. et al. 2002. Fibroblast growth factor 5 inhibits hair growth by blocking dermal papilla cell activation. Biochemical and Biophysical Research Communications 290: 169-176. specif. p. 169.*
Yang, C-C et al. 2010. Review of hair follicle dermal cells. Journal of Dermatology Science 57: 1-19. specif. p. 2.*
Egusa, H. et al. 2010. Gingival fibroblasts as a promising source of induced pluripotent stem cells. PLoS One 5(9): 1-12. specif. pp. 1, 5, 6.*

(Continued)

*Primary Examiner* — Renee Claytor
*Assistant Examiner* — Sharon M. Papciak
(74) *Attorney, Agent, or Firm* — Browdy and Neimark, PLLC (57) ABSTRACT

The present invention relates to the use of gingival fibroblast-derived products to reduce hair loss and promote hair growth. Specifically, the invention relates to a product derived from gingival fibroblasts to be used in the treatment or prevention of alopecia, as well as in the promotion of natural hair growth and/or in the control of natural hair loss.

6 Claims, 4 Drawing Sheets

(56) References Cited

OTHER PUBLICATIONS

Ebisawa, K. et al. 2011. Gingival and dermal fibroblasts: Their similarities and differences revealed from gene expression. Journal of Bioscience and Bioengineering 111(3): 255-258. specif. pp. 255, 256.*

Hoffman, R.M. et al. 2006. The pluripotency of hair follicle stem cells. Cell Cycle 5(3): 232-233. specif. p. 232.*

Schneider M R et al.,"The Hair Follicle as a Dynamic Miniorgan" Current Biology, pp. R132-R142, vol. 19, No. 3 (Feb. 2009).

Paus et al., "Therapeutic strategies for treating hair loss" Drug Discovery Today: Therapeutic Strategies, pp. 101-110, vol. 3, No. 1 (Apr. 2006).

Ebisawa K et al.,"The Expression Profile of Anti-Aging Related Genes in Dermal and Gingiva Fibroblasts", Annals of Nutrition and Metabolism: European Journal of Nutrition. Metabolic Diseases and Dietetics, S. Karger AG, pp. 409-415, vol. 51 (Nov. 2007).

Rogers N E et al., "Medical treatments for male and female pattern hair loss", Journal of the American Academy of Dermatology, pp. 547-566, vol. 59, No. 4 (Oct. 2008).

Leyden J et al., "Finasteride in the treatment of men with frontal male pattern hair loss". Journal of the American Academy of Dermatology, pp. 930-937, vol. 40, No. 6 (Jun. 1999).

Gölz et al., Differences in human gingival and dermal fibroblasts may contribute to oral-induced tolerance against nickel, J Allergy Clin Immunol, 138(4):1202-105.e3 (2016).

Middelkoop, Fibroblast Phenotypes and Their Relevance for Wound Healing, Lower Extremity Wounds, 4(1):9-11 (2005).

* cited by examiner

USE OF GINGIVAL FIBROBLASTS IN THE TREATMENT OF ALOPECIA

The present invention relates to the use of gingival fibroblasts or derived products to limit hair/body hair loss and/or to promote their growth. More particularly, the invention relates to a gingival fibroblast-derived product for its use in the treatment or prevention of alopecia and in promoting natural hair growth and/or fighting natural hair loss.

Hair growth and hair renewal are mainly determined by the activity of hair follicles. In human beings, hair follicles have, as in mice and other furbearing mammals, a renewal cycle comprising three phases: anagen, catagen and telogen. The anagen phase, or growth phase, lasts many years and is associated to hair growth. It is followed by a catagen phase or transition phase, which lasts about 3 weeks, then a telogen, or rest phase, at the end of which the old hair falls out and is replaced by a new follicle in anagen phase (Cotsarelis and al., Trends in Molecular Medicine, Vol. 7 No. 7, 2001). The hair is thus constantly renewing and most of the 100000 to 150000 hairs of a head hair are in the growth phase (i.e. about 85% in the anagen phase, 2% in the telogen phase and more than 10% in the loss phase). On average, a human being loses about 50 to 150 hairs a day, this «normal» loss generally prevailing at the end of the summer and during springtime (to reach about 175 hairs lost per day). A loss of more than 100 to 150 hairs per day is considered as pathological if it lasts for an extended period of up to two months.

The term alopecia means partial or general hair loss. Many factors may be involved in alopecia such as genetic factors, age, sex, disease, stress, hormonal problems, side effects of medications, scars. It is possible to distinguish several forms of alopecia:

- Hereditary androgenic alopecia: it is the most common. Early hair loss occurs in genetically predisposed subjects and affects mostly men. It is manifested by a decrease in the volume of hair, possibly baldness, and affects 50% of men more than 50 years old (Yazdan P. Semin Cutan Med Surg 2012; 31:258-266);
- Postmenopausal alopecia: this is the most common cause of baldness in women. In women, hair loss is more diffuse and expanded than in men. Female diffuse alopecia is a disorder that often begins with menopause and which affects approximately 40% of women aged more than 70 years old (Yazdan P. Semin Cutan Med Surg 2012; 31:258-266). The term diffuse shows that, in contrast to men, hair loss affects the entire scalp in an uniform manner;
- Acute alopecia: it can be linked to chemotherapeutic treatment, stress, significant nutritional deficiencies, iron deficiency, hormonal disorders;
- Scarring alopecia: it can be caused by skin problems (tumours, burns, alopecia aeata), acute irradiation, lupus erythematosus or parasites (ringworm, lichen);
- Alopecia areata: it seems to be autoimmune and characterized by bald spots of varying sizes and location; and
- Congenital alopecia: rare, it corresponds to a lack of root or to hair abnormalities (mutations).

Alopecia is essentially linked to a disruption in hair renewal which leads, at first, to an increase of the frequency of cycles at the expense of hair quality and then hair quantity. The most common phenomenon is a reduction of the growth cycle (anagen phase) due to a halt in cell proliferation. This results in a premature induction of the catagen phase and a greater number of hair follicles in the telogen phase and consequently to a greater hair loss. To fight hair loss, it is thus necessary to revive the hair cycle, for example, by activating the anagen phase.

The cosmetic and pharmaceutical industries have sought for many years compositions able to stop or reduce alopecia, in particular androgenic alopecia, but also to stimulate natural hair growth and/or to slow their loss for purely aesthetic reasons, especially in individuals unaffected by alopecia nevertheless wishing to have thicker and/or longer head hair.

The treatment of alopecia and natural hair growth promotion have been the subject of many studies, and several products or techniques are available.

The literature reports numerous compounds intended for treating or preventing alopecia and for restoring or promoting hair and body hair growth. By way of example, finasteride (Propecia®) is capable of stabilising hair loss and, in some cases, of allowing a more or less significant regrowth. However, this compound has many undesirable side effects such as decreased libido or depression. Minoxidil (Rogaine®) is, for its part, another composition marketed to treat baldness. However, it appears that hair grown thanks to the product fall when application of the product is stopped.

Cosmetic agents intended to impart volume to fine hair are also marketed, particularly in shampoos. However, they do not stimulate hair growth, and their effect also ceases upon interruption of their use.

Micro-transplantation methods of have also been developed. This technique involves taking hair grafts on the crown (or in the eternal hair) and transplanting them on the top of the head. Nevertheless, some grafts may fall 2-4 weeks after transplantation and this technique requires several interventions to be effective.

Stem cells have recently received particular attention due to their ability to regenerate tissues and organs. Thus, an alternative method would be to introduce stem cells capable of differentiating into a hair follicle in order to promote hair growth on human skin (US2008254006).

Thus, despite many developments regarding this issue, there remains a need for new treatments capable of accelerating the growth/slowing the loss of hair and/or body hair and of increasing the density of hair follicles, either in the frame of alopecia or of the natural loss of hair and/or body hair. These needs are fulfilled by the present invention described below.

SUMMARY OF THE INVENTION

The present invention follows from the unexpected finding, by the inventors, that the administration of gingival fibroblasts can to significantly stimulate the growth of head hair or other hairs.

Thus, the invention relates to a gingival fibroblast-derived product for its use in the treatment or prevention of alopecia. More particularly, the invention relates to a gingival fibroblast-derived product for its use in the treatment or prevention of hereditary androgenic alopecia, postmenopausal alopecia, acute alopecia or alopecia areata.

The invention also relates to a gingival fibroblast-derived product, for its use in the treatment or prevention of alopecia, administered intradermally or topically.

In another aspect, the present invention relates to the cosmetic use of a gingival fibroblast-derived product to limit hair/body hair loss and/or to promote their growth and/or to increase the density of hair follicles. More particularly, this use allows promoting hair growth and increasing the density of hair follicles. Preferably, this cosmetic use aims at fighting natural hair/body hair loss and/or at stimulating their natural growth and/or natural density.

In a preferred aspect, the present invention relates to the cosmetic use of a gingival fibroblast-derived product to limit hair/body hair loss and/or to promote their growth and/or to increase the density of hair follicles in an individual showing the consequences of alopecia.

In another embodiment, the present invention also relates to a method for limiting hair/body hair loss and/or promoting their growth and/or increasing the density of hair follicles comprising a step of administering a gingival fibroblast-derived product to an individual.

More particularly, this method of treatment comprises or consists of the following steps:
  taking gingival fibroblasts from an individual,
  eventually culturing the gingival fibroblasts,
  obtaining a gingival fibroblast-derived product
  administering the gingival fibroblast-derived product to the individual According to the present invention the gingival fibroblast-derived product is selected from the group consisting of i) gingival fibroblasts, for example directly taken from the gingival tissue, ii) gingival fibroblasts from a culture, iii) a gingival fibroblast extract and, iv) a gingival fibroblast conditioned medium.

The present invention may be used in association with known treatments for alopecia or with molecules known to promote hair/body hair growth or to limit their loss such as finasteride or minoxidil, or to benefit to an individual who has undergone or is to undergo a hair transplantation.

DESCRIPTION OF THE FIGURES

FIG. 4. Higher efficiency of human gingival fibroblasts compared to MSCs to promote epidermal growth. Analysis of mRNA factors considered as proliferation markers (A; Ki67), or promoting the proliferation of keratinocytes (B; EGF & KGF), 49 days after irradiation (30 Gy) in the skin of animals transplanted 21 days after irradiation showed a stimulation of their expression by human gingival fibroblasts ($1.5.10^6$ transplanted cells). This stimulation is absent for MSCs ($2.5.10^6$ transplanted cells). (A)—Ki67 is a nuclear protein required for cell proliferation. The expression of its mRNA declines 1 week after gamma irradiation even if it then returns to a value close to that existing in the non-irradiated skin. Only the grafting of gingival fibroblasts stimulates its expression later after irradiation (49 days) which shows that cell multiplication is essential for the reorganization of the injured area. (B)—Only human gingival fibroblasts can restore a level of expression of EGF (Epidermal growth factor) comparable to that of a non-irradiated skin 49 days after irradiation. For KGF (keratinocyte growth factor or FGF-7), only the gingival fibroblasts still stimulate its expression 49 days after irradiation. Both factors are important for the growth of keratinocytes participating to the organization of inter-follicular epidermis but also to the proliferation of keratinocytes of hair follicles.

DETAILED DESCRIPTION OF THE INVENTION

The present invention relates to the use of a gingival fibroblast-derived product to limit hair/body hair loss and/or to promote their growth. The invention also relates to a gingival fibroblast-derived product to treat or prevent alopecia and their use to promote the natural growth of hair and/or to slow down normal hair loss in individuals not afflicted with alopecia.

As intended herein, the expression "hair/body hair" relates to the head hair, the body hairs, eyebrows, eyelashes and/or coat. Preferably, "hair/body hair" means the head hair.

Thus, within the frame of the present invention, the term "subject" or "individual" preferably refers to a mammal, more preferably a human. The individual may also be a pet, such as a cat, a dog, a ferret, and a rabbit.

As intended herein, the term "alopecia" relates to the total or partial loss of hair/body hair, for example related to the reduction of hair growth and/or the acceleration of hair/body hair loss. This term includes, but is not limited to, hereditary androgenic alopecia, postmenopausal alopecia, acute alopecia, scarring alopecia, alopecia areata, and congenital alopecia. The consequences of alopecia are a temporary or permanent and partial or total absence of hair.

As intended herein, the expression "treatment" or "treating alopecia" relates to alopecia stopping, alopecia reduction and/or alopecia alleviation. Thus, "treating alopecia" includes limiting hair loss, promoting hair growth, increasing the density of hair follicles and/or regulating the hair follicle cycle phases. In other words, such a treatment is aimed at an individual afflicted with alopecia.

As intended herein, the expression «preventing» or «prevention of alopecia» relates to reducing the risk of developing alopecia, or to slowing down the progress of alopecia in a mammal that is likely to develop alopecia. In other words, prevention is aimed at an individual afflicted with alopecia.

As intended herein, the expression "natural hair/body hair loss" or "normal hair/body hair loss" relates to hair/body hair loss normally seen in a subject with a physiologically normal hair cycle (i.e. healthy). Preferably, said loss is at most of one hundred hairs per day. More preferably, said subject is not afflicted with alopecia.

As intended herein, the expressions "natural hair/body hair growth" or "normal hair/body hair growth" relates to a hair/body hair growth usually seen in a subject with a physiologically normal hair cycle (i.e. healthy). Preferably, said subject is not afflicted with alopecia.

As intended herein, the expression "natural density of hair follicles" relates to a density of hair follicles usually observed in a subject having a physiologically normal hair cycle. Thus in a humans being, depending on the hair cycle and the of hairs in the anagen/telogen phase, said density varies depending on the zone of the body considered, with an average of 200 to 300 hairs/cm$^2$ on the scalp, 50 hairs/cm$^2$ on the face and 10 hairs/cm$^2$ on the rest on the body. Preferably, said subject is not afflicted with alopecia.

As intended herein, the expression "limiting" or "slowing down" means slowing down, reducing, and/or stopping. Thus, by "limiting or slowing down hair/body hair loss" it is intended to mean slowing, reducing, or even stopping, hair/body hair loss.

As intended herein, the term "promoting", "stimulating" or "increasing" means to expanding, enhancing and/or accelerating. Thus, by "promoting or stimulating hair/body hair growth" it is intended to mean expanding, enhancing and/or accelerating hair and/or body hair growth.

In accordance with the invention, "gingival fibroblasts" relate to mesenchymal cells found in the soft connective tissues of the gum which can remodel it and repair it thanks to their synthesis, migration, adhesion and proliferation properties. Gingival fibroblasts are notably described in Gogly et al., (1997) Clin. Oral Invest. 1:147-152; Gogly et al. (1998) Biochem. Pharmacol. 56:1447-1454; and Ejeil et al. (2003) J. Periodontol. 74:188-195.

As intended herein, the expression "gingival fibroblast-derived product" relates to any product which can be obtained from gingival fibroblasts in themselves or which contains gingival fibroblast secretions. It is thus preferred that the gingival fibroblast-derived product according to the invention is selected from the group consisting of i) gingival fibroblasts, for example directly collected from the gingival tissue, ii) gingival fibroblasts from a culture, iii) a gingival fibroblast extract and, iv) a gingival fibroblasts conditioned medium.

Gingival fibroblast cultures useful for the implementation of the present invention can be obtained by conventional techniques, which are known by one of skill in the art (Barlovatz-Meimon and al., Culture of Animal Cells, p. 898 ill. Paris. INSERM 2003). The gingival fibroblast extract according to the invention can be obtained by any cell fragmentation method known in the art. In particular, the gingival fibroblast extract according to the invention can be a membrane extract, a cytoplasmic extract or a nuclear extract.

The gingival fibroblast conditioned medium according to the invention relates to any medium which has been contacted by gingival fibroblasts. The medium can be a liquid cell culture medium for instance the "Dulbecco's Modified Eagle Medium", or preferably a culture medium without serum such as the medium described in EP1972685, U.S. Pat. No. 7,951,593 and CN102747033. Preferably, the medium has been contacted by gingival fibroblasts for a time sufficient for the gingival fibroblasts to have secreted in the medium. By way of example, the medium has been contacted by gingival fibroblasts during 1 to 7 days, preferably 1 day and more preferably 1 day in a medium without serum. The conditioned medium according to the invention preferably contains molecules secreted by the cells such as constituents of the extracellular matrix, growth factors and cytokines. Preferably, the conditioned medium contains no cellular debris.

In a preferred embodiment, the gingival fibroblast-derived products according to the invention contain living cells that allow a long lasting action. This embodiment is particularly preferred within the frame of the prevention or treatment of alopecia. The presence of living cells is nevertheless rather undesirable in the cosmetic field. Accordingly, in another preferred embodiment of the invention, the gingival fibroblast-derived products according to the invention do not contain living cells, more advantageously in the frame of the fight against hair/body hair natural loss and/or the natural promotion of their growth, and/or the increase of the natural density of hair follicles.

When the gingival fibroblast-derived products are gingival fibroblasts, for example directly collected from the gingival tissue (i), they may be obtained by suspending gingival fibroblasts in a physiologically acceptable medium directly after sampling from an individual or after a culturing step as described above.

As shown in the examples, this invention relies on experiments conducted by the inventors on the effectiveness of gingival fibroblasts in the treatment of alopecia and in particular of mesenchymal stromal cells (MSCs) from bone marrow and gingival fibroblasts. More particularly, this invention relies on the unexpected finding by the inventors of the superior efficiency of gingival fibroblasts and gingival fibroblast-derived products compared to mesenchymal stromal cells for promoting hair/body hair growth, increasing the density of hair follicles and regulating hair follicle cycle phases.

Indeed, in in vivo tests, the inventors have shown that the administration of a suspension of human gingival fibroblasts on irradiated skin, on a recent or established lesion, resulted in a dense and uniform hair growth in a few weeks. More surprisingly still, the comparison of the effectiveness of human gingival fibroblasts to that of MSC showed that hair length was significantly improved by gingival fibroblast-derived products with respect to MSCs.

A thorough study of the mechanisms involved in this accelerated regrowth showed that the effect of MSCs and gingival fibroblasts or gingival fibroblast-derived products on matrix-remodelling and inflammation molecular markers of was similar. In contrast, the gingival fibroblasts or the gingival fibroblast-derived products have an improved effect compared to MSCs on the differentiation of the epidermis and the control of its thickness. This induces a stimulation of hair follicles, which are then able to generate a faster growth of hair/body hairs.

The applications of gingival fibroblast-derived products according to the invention aim at limiting hair/body hair loss, and/or promoting their growth and/or increasing the density of hair follicles, particularly in a subject afflicted with alopecia or in a subject with a physiologically normal hair cycle.

The present invention thus relates in a first aspect to a gingival fibroblast-derived product for its use in the treatment or the prevention of alopecia. More particularly, the present invention relates to a gingival fibroblast-derived product, as a medicament, for the treatment or the prevention of alopecia.

According to another aspect, the invention relates to a combination of the gingival fibroblast-derived product as defined above and at least one anti-hair-loss agent for a simultaneous, separate or sequential use for the prevention or the treatment of alopecia. Particularly preferred anti-hair-loss agents according to the invention are finasteride and minoxidil.

According to another aspect, the present invention relates to a composition comprising a gingival fibroblast-derived product for its use in the treatment or prevention of alopecia. Preferably, said composition further comprises at least one anti-hair-loss agent as defined above. The present invention relates also to the use of a gingival fibroblast-derived product for the manufacture of a composition for treating or preventing alopecia.

As indicated above, the present invention aims at limiting hair/body hair loss and/or promoting their growth and/or increasing the density of hair follicles. The gingival fibroblast-derived products according to the invention may in particular be used for a purely aesthetic purpose.

Thus, another aspect of the present invention relates to the cosmetic use of a gingival fibroblast-derived product to limit hair/body hair loss and/or to promote their growth and/or to increase the density of hair follicles. Preferably, said hair loss and/or hair growth and/or density of hair/body hairs are natural according to the above definitions. Preferably still, the subject is not afflicted alopecia.

The present invention also relates to the cosmetic use of a gingival fibroblast-derived product in a composition to limit hair/body hair loss and/or to promote their growth and/or to increase the density of hair follicles. Preferably, said hair loss and/or growth and/or density of hair/body hairs are natural according to the above definitions. Preferably still, the subject is not afflicted with alopecia.

Preferably, the present invention relates to the cosmetic use of a gingival-fibroblast-derived product in a composition for promoting the growth of hair/body hairs and/or increasing the density of hair follicles. Preferably, said growth and/or density of hair/body hairs are natural according to the above definitions. Preferably still, the subject is not afflicted with alopecia.

Within the frame of a cosmetic use of a gingival fibroblast-derived product, said derive product is preferably iv) a gingival fibroblast conditioned medium. Preferably, for this use, said gingival fibroblast conditioned medium does not comprise living cells.

Alternatively, in a preferred embodiment, the present invention relates to the cosmetic use of a gingival fibroblast-derived product in an individual exhibiting a partial or total absence of hair/body hair. This partial or total absence of hair/body hair may correspond to the consequences of alopecia. The partial or total absence of hair/body hair may also correspond to the consequences of surgery.

The present invention also refers to a method for limiting hair/body hair loss and/or promoting their growth and/or increasing the density of hair follicles comprising a step of administering a gingival fibroblast-derived product to an individual. In the context of the present invention, said individual may be preferably a subject afflicted with alopecia, or a subject whose hair cycle is physiologically normal.

Preferably, the invention relates to a method for promoting hair growth comprising a step of administering a gingival fibroblast-derived product to an individual.

More preferably, the method according to the present invention comprises or consists of the following steps:
taking gingival fibroblasts from an individual,
culturing the gingival fibroblasts,
obtaining a gingival fibroblast-derived product, and
administering the gingival fibroblast-derived product.

In a particularly preferred aspect, the present invention relates to a method of treatment of alopecia comprising a step of administering a gingival fibroblast-derived product to an individual. The preferred embodiments are as defined above.

In another preferred embodiment, the present invention relates to a method for promoting natural hair/body hair growth, and/or limiting hair/body hair loss, and/or increasing the natural density of hair follicles, comprising a step of administering a gingival fibroblast-derived product to an individual. The preferred embodiments are as defined above The composition according to the invention comprises a gingival fibroblast-derived product (cells, extract and/or conditioned medium) in a quantity sufficient to obtain the desired effect. The intended effect according to the invention is to limit hair/body hair loss, to promote their growth, to increase the density of hair follicles and/or to regulate hair follicle cycle phases.

When the a gingival fibroblast-derived product comprises cells, the latter are at a concentration comprised between 0.25 and $5.10^6$ cells/mL and more preferably between 1.5 and $2.5 \times 10^6$ cells/mL.

One of the surprising aspects of the invention lies in the fact that gingival fibroblast-derived products are much more effective for the stimulation of hair follicles than other products comprising mesenchymal cells, in particular bone marrow MSCs. Bone marrow MSCs comprise about 10% of progenitor cells (Umbilical Cord Blood, ISBN: 978-981-283-329-7; Chap. 9 M Prat-Lepesant et al.) while gingival fibroblasts according to the invention comprise a maximum of 3% of progenitor cells (Fournier B P et al., (2010) Tissue Eng Part A. 16(9):2891-9). Accordingly, this effect does not follow from a greater number of progenitor cells in the products of the invention.

In a specific embodiment, the gingival fibroblast-derived products may further comprise progenitor cells, preferably less than 20, 10% or 5%.

In a specific embodiment, the gingival fibroblasts may for example be those described in Fournier B P and al., (2010) Tissue Eng Part A. 16(9):2891-9.

The mode of administration depends on the derived product and on the localisation of the treated area.

According to an aspect of the invention, the gingival fibroblast-derived product is present in a composition suitable for intradermal or topical administration for the scalp and skin, containing a physiologically acceptable medium.

A composition "suitable for topical administration" can in particular be in the form of an aqueous solution, of a liquid or semi-liquid emulsion obtained by dispersing a fatty phase in an aqueous phase or vice versa, or of a micro-emulsion, of micro-capsules, of micro-particles. The pH of a composition according to the invention, when it comprises at least one aqueous phase, is preferably between 4 and 9, preferably between 4 and 7, advantageously from 5 to 6.

A "physiologically acceptable medium" is, according to the invention, a cosmetically or pharmaceutically acceptable medium compatible with the skin, mucous membranes, human hair and/or mammalian fur.

Preferably, the individual according to the invention is a mammal, more preferably it is a human. The individual may also be a pet such as a cat, a dog, a ferret, a rabbit.

Procedures to collect, grow and store gingival fibroblasts are well known to one of skill in the art and are described in particular in Naveau et al. (2006) J. Periodontol. 77:238-47 and in Gogly et al. (2007) Arterioscler. Thomb. Vasc. Biol. 27:1984-1990.

Gingival fibroblasts may be heterologous, that is to say obtained from an individual of a different species. Preferably, the gingival fibroblasts used according to the invention are allogeneic, that is obtained from another individual of the same species. Even more preferably, the gingival fibroblasts used according to the invention are autologous, that is they are taken from the individual to whom the gingival fibroblast-derived product is to be administered. Advantageously, gingival fibroblasts provide for an almost limitless source of autologous fibroblasts.

Advantageously, gingival fibroblasts are easily sampled and cultured. Besides, gingival fibroblasts possess a high growth speed.

Advantageously, gingival fibroblasts are more effective to stimulate hair/body hair growth than other fibroblasts or mesenchymal cells, in particular bone marrow MSCs. The use of a gingival fibroblast-derived product according to the invention is preferably implemented on areas of the scalp exhibiting abnormal hair loss or a lack of hair. The identification of these areas is easily performed before the use, or the administration, of the gingival fibroblast-derived product according to the invention.

The administration to an individual as defined above of a gingival fibroblast-derived product according to the invention, preferably near or at a body site to be treated, can be performed by any method known in the art. For example, by scalp injection using microneedles.

The composition according to the invention is a composition for intradermal or topical administration. Advantageously, the gingival fibroblast-derived product is present in a composition suitable for intradermal application containing a physiologically acceptable medium.

It is preferred that the gingival fibroblast-derived product or the composition comprising said product is administered by subcutaneous or intramuscular injection.

In addition, the gingival fibroblast-derived product may be administered alone (in solution or in suspension) or associated to a support (e.g. encapsulated in microcapsules).

According to the invention, although being effective by itself, the gingival fibroblast-derived product may be used in association with known alopecia treatments or with molecules known to promote hair/body hair growth or to limit their loss. By way of example, the gingival fibroblast-derived product can be used in association with finasteride or minoxidil.

Preferably, according to the present invention, the gingival fibroblast-derived product can be used before, during or after a micro-transplantation. Micro-transplantation methods are well known in the art (M J Kristine Bunagan et al 2013 Dermatologic Clinics, 31:1 p 141-153) and could advantageously benefit from the effect of a gingival fibroblast-derived product on hair/body hair growth and on the density of hair follicles. Indeed, the administration of a gingival fibroblast-derived product according to the invention through its effect on hair/body hair growth and the density of hair follicles can lead to a higher efficiency of micro-transplantation.

The gingival fibroblast-derived product according to the invention can be used, for example, from one month before to one month after a hair transplantation, preferably from 15 days before to 15 days after a hair transplant.

EXAMPLE

Material and Methods

Cell Culture

The gingival fibroblasts are obtained from healthy donors. After enzymatic dissociation of gum biopsies (collagenase, dispase), gingival fibroblasts are cultured in a medium without serum in the presence of platelet lysate (Doucet and al, J Cell Physiol 2005; 205 (2):228-36).

MSCs are collected from the bone marrow of healthy donors. MSCs are cultured in a medium without serum in the presence of platelet lysate (Doucet and al, J Cell Physiol 2005; 205 (2):228-36).

After amplification, the gingival fibroblasts and/or MSCs are detached from their culture support and are suspended insaline before being injected subcutaneously and intramuscularly at the lesion site.

Mice Model

The hind legs of NOD/SCID immunocompetent mice (allowing human cell transplantation) were irradiated (25-30 Gy) (BENSIDHOUM and al, J Soc Biol 2005; 199 (4):337-41).

Transplantation

According to the experiment, the treatment was carried out on an acute (1 day after irradiation) or established lesion (21 days after irradiation). Each experiment generally comprised 5 animals per lesion type.

The cells were injected subcutaneously and intramuscularly at several points in the lesion area (15 to 20 points). The volume of the cellular suspension was 200 µL (Saline). The dose effect of gingival fibroblasts was studied by injecting $2.5 \times 10^6$, or $1.5 \times 10^6$ or $0.5 \times 10^6$ cells per mice. A single concentration was selected for the MSCs ($2.5 \times 10^6$) corresponding to the concentration used in human clinical setting for the treatment of accidental irradiations (Lataillade et al., Regen Med 2007; 2(5):785-94. Bey. et al., Wound Repair Regen. 2010; 18 (1):50-8).

Analyses

The animals were monitored during 4 to 6 weeks (depending on the experience). The animals were sacrificed at the end of the experiment for analysis. Depending on the experiment, an intermediate stop (1 week after cell therapy) was performed on some of the animals.

The "macroscopic" follow-up consisted in a regular observation of animals by taking photographs of the injured area.

After sacrificing the animals, the irradiated tissues were collected. A part was used for histological analysis, the other was used to carry out an extraction allowing the analysis of mRNA expression.

Results and Conclusions

Figure 1:
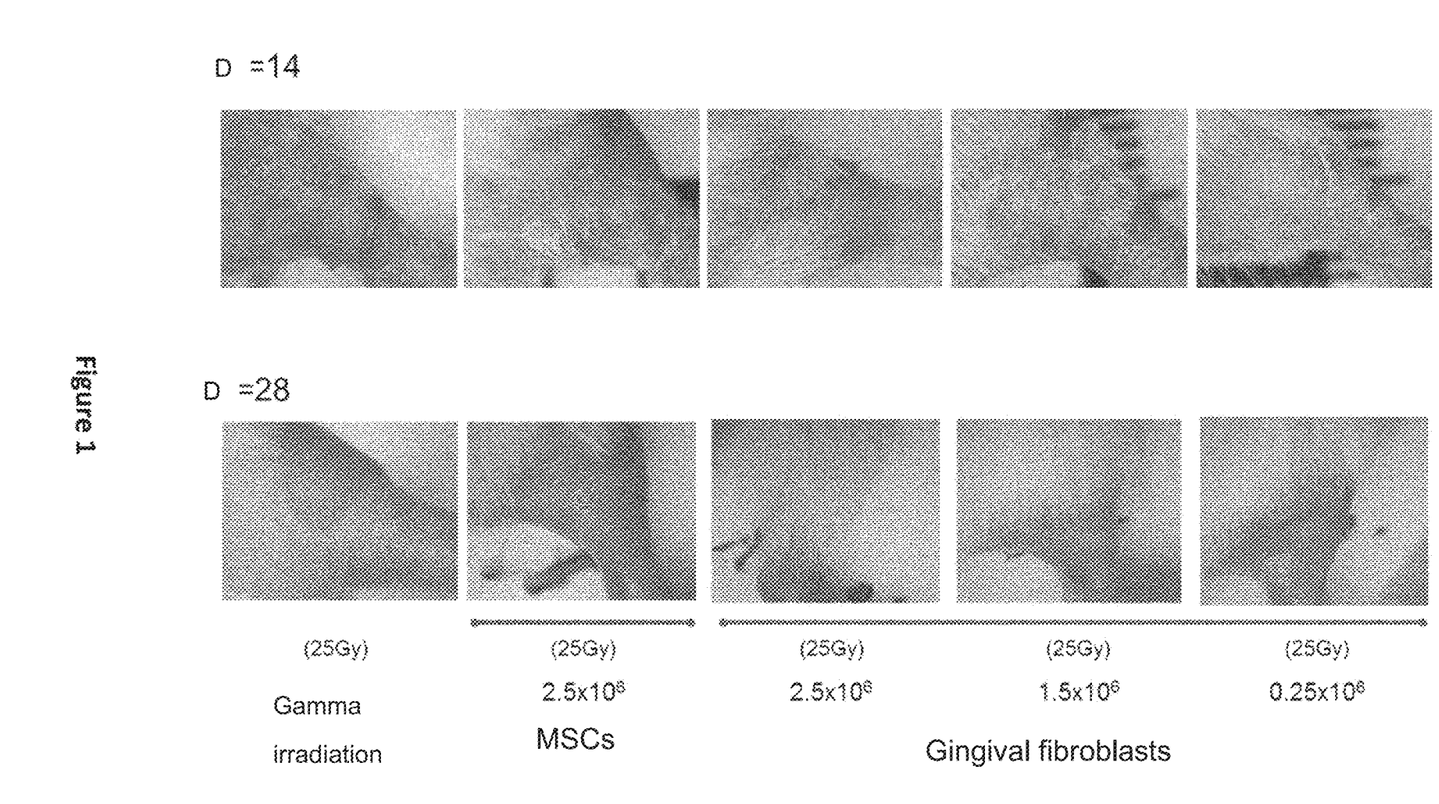
FIG. 1, Higher efficiency of human gingival fibroblasts compared to mesenchymal stromal cells (MSCs) to promote hair growth. Observation of animals 28 days after gamma irradiation (25 Gy) of the hind leg of NOD/SCID mice transplanted the day after irradiation shows that all three concentrations of human gingival fibroblasts used stimulate coat regrowth. MSCs from human bone marrow are not as effective.

The "macroscopic" observation shows an improvement of the treated lesion by gingival fibroblasts and MSCs, whether the treatment has been performed on an acute lesion or on an established lesion. A significant regrowth of hair is observed in the presence of gingival fibroblasts (FIG. 1). MSCs do not induce such an effect on coat regrowth.

Figure 2:
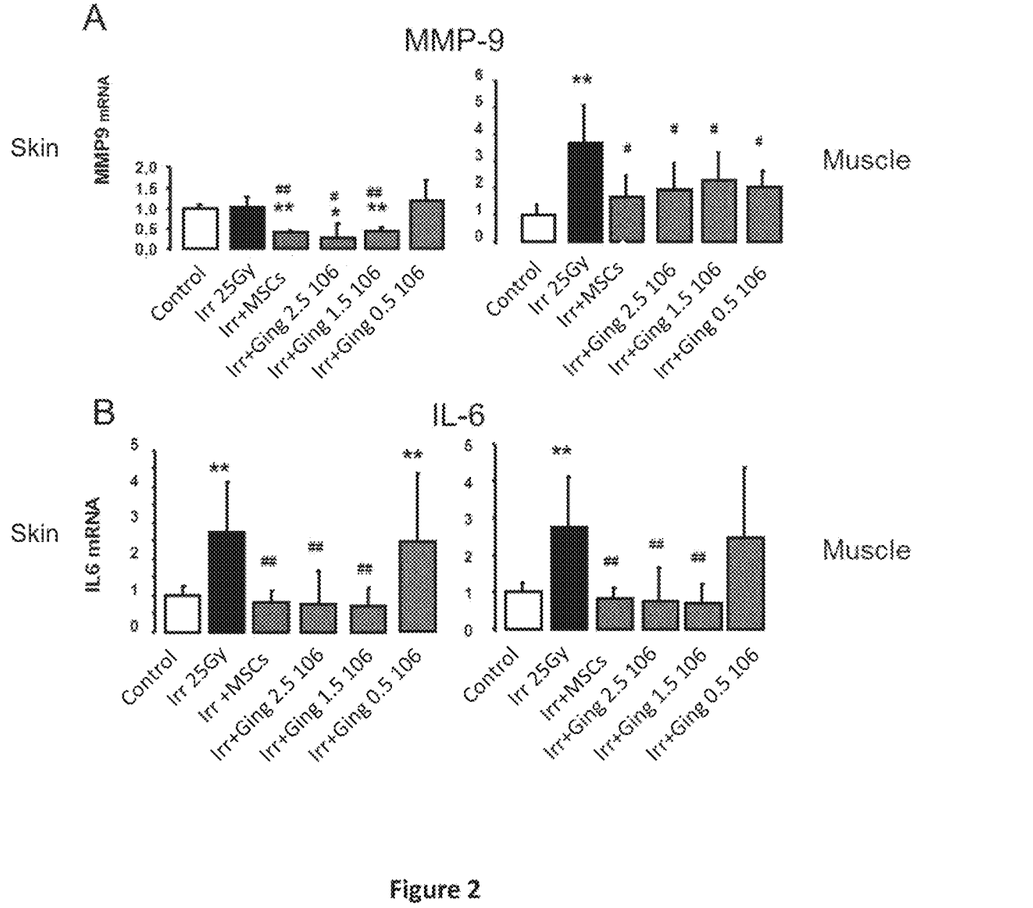
FIG. 2. Similar effect of human gingival fibroblasts and MSCs on the control of inflammation and the regulation of remodelling of the dermis matrix. The analysis of MMP-9 (FIG. 2A) and IL-6 (FIG. 2B) mRNA expression, 40 days after irradiation (25 Gy) in the skin and muscles of animals transplanted the day after the irradiation shows no significant differences between MSCs ($2.5 \times 10^6$ transplanted cells) and the two highest concentrations of human gingival fibroblasts ($2.5 \times 10^6$ and $1.5 \times 10^6$ transplanted cells). Thus, MSCs and gingival fibroblasts inhibit comparably the radiation-induced induction of the expression of MMP-9 (Matrix Metalloproteinase 9; involved in the degradation of the extracellular matrix) and IL-6 (interleukin 6; involved in the inflammatory process).

MMP-9 and IL-6 mRNA expression is not different for gingival fibroblasts and MSCs, demonstrating that both cell types are effective to stimulate dermis remodelling and to inhibit the inflammatory process (FIG. 2).

Figure 3:
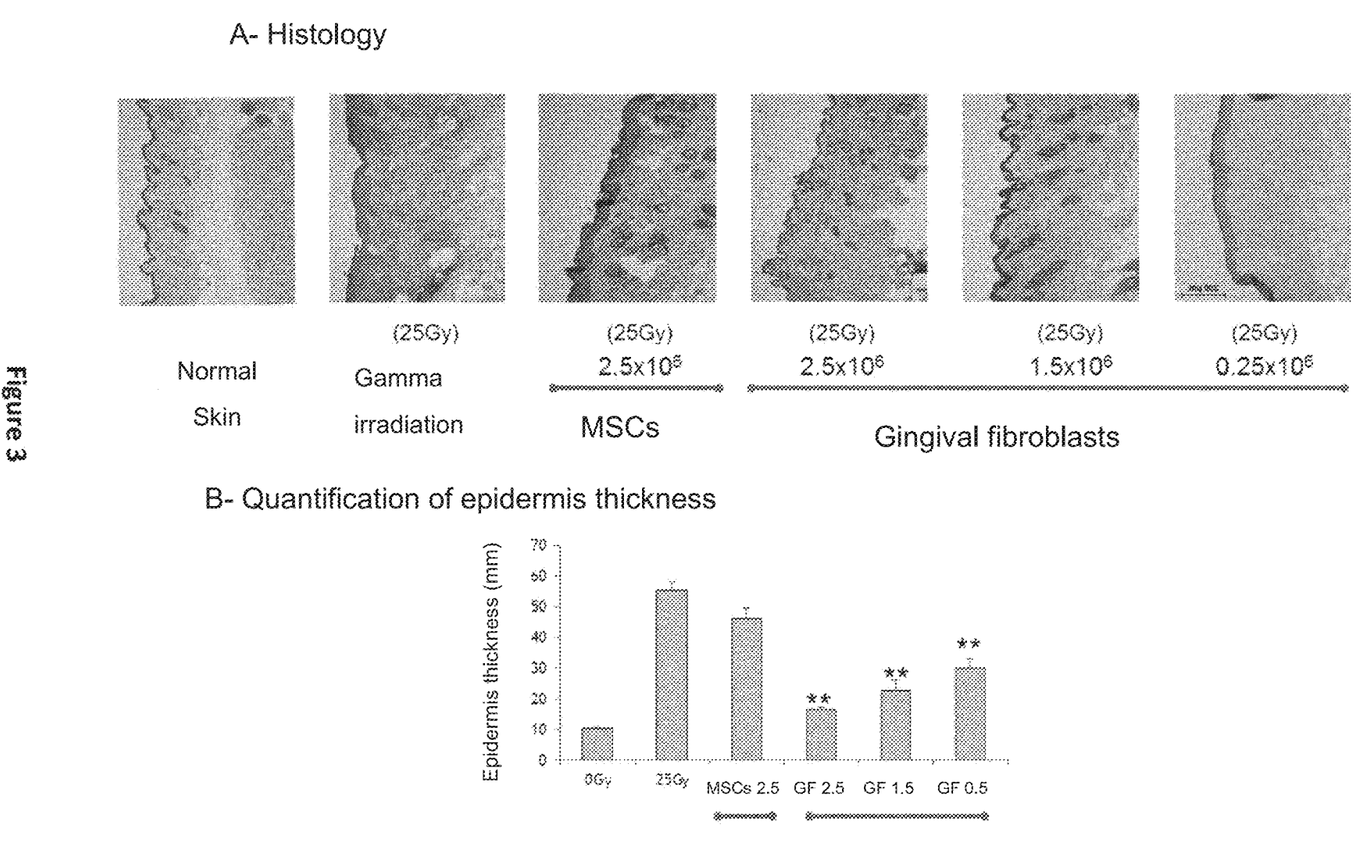
FIG. 3. Higher efficiency of human gingival fibroblasts compared to MSCs on the regulation of epidermal differentiation. Histological analysis (A) 40 days after irradiation (25 Gy) in the skin of animals transplanted the day after irradiation shows a decrease of the thickening radiation-induced of the epidermis by human gingival fibroblasts. Which is not the case for the MSCs. Quantification of epidermal thickness (B) shows that this regulatory effect of epidermal differentiation by gingival fibroblasts is dose dependent.

The histological analysis shows that human gingival fibroblasts regulate the thickness of the epidermis by inhibiting the radiation-induced increase in thickness (FIG. 3). The MSCs do not regulate this differentiation of the epidermis.

Figure 4:
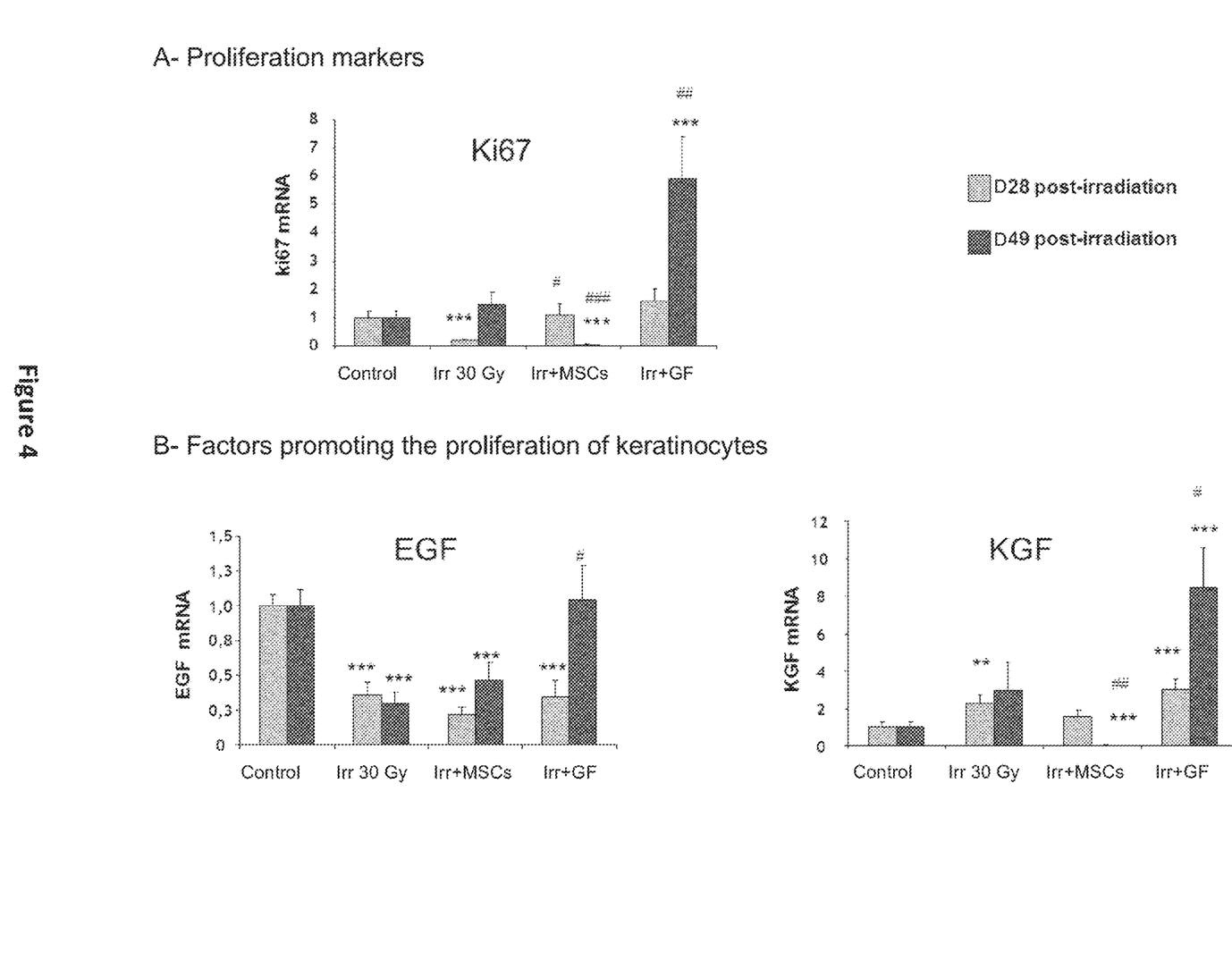

The stimulation of the expression of Ki 67 (marker of proliferative activity) only after transplantation of gingival fibroblasts shows they strongly and lastingly contribute to the stimulation of cellular divisions necessary for tissue remodelling (FIG. 4-A). MSCs do not contribute to such an intense and lasting stimulation (FIG. 4-B).

Gingival fibroblasts also stimulate the expression of EGF in a lasting way, allowing to regain the level of expression of non-irradiated skin. The stimulation of this factor in the lesion contributes to the stimulation of cellular divisions necessary to reorganize the tissues. MSCs do not contribute to such an intense and lasting stimulation (FIG. 4-B).

Finally, the stimulating action of gingival fibroblasts on KGF expression of demonstrates an action on the epidermis especially on keratinocytes, since this factor has no stimulating effects on the growth of dermal fibroblasts (Rubin and al, Proc Natl Acad Sci USA. 1989; 86(3):802-6) (FIG. 4-B).

As a conclusion, unlike MSCs from human bone marrow, human gingival fibroblasts strongly stimulate hair regrowth. This effect is related to a broader action on the epidermis. Gingival fibroblasts also stimulate the expression of factors favouring the proliferation of epidermal cells and especially of keratinocytes in a lasting way.

The invention claimed is:

1. A method for limiting hair/body hair loss and/or promoting the growth of hair/body hair and/or increasing the density of hair follicles in an individual, comprising administering an effective quantity of a gingival fibroblast-derived product to the individual to limit hair/body hair loss and/or to promote the growth of hair/body hair and/or to increase the density of hair follicles in the individual.

2. The method according to claim 1, wherein the hair loss and/or hair growth and/or density of hair follicles are natural.

3. The method according to claim 1, wherein the gingival fibroblast-derived product is selected from the group consisting of gingival fibroblasts, gingival fibroblasts from a culture, a gingival fibroblast extract and a gingival fibroblast conditioned medium.

4. The method according to claim 1, wherein the gingival fibroblast is heterologous, autologous or allogeneic.

5. The method according to claim 1, wherein the gingival fibroblast-derived product is administered in association with at least one anti-hair loss agent.

6. The method according to claim 1, wherein the gingival fibroblast-derived product is administered in association with at least one anti-hair loss agent selected from the group consisting of finasteride and minoxidil.

* * * * *